United States Patent
Guo et al.

(10) Patent No.: US 9,913,933 B2
(45) Date of Patent: Mar. 13, 2018

(54) MULTILAYERED CATHETER SHAFT CONTAINING POLYVINYLIDENE FLUORIDE POLYMERS

(71) Applicant: St. Jude Medical, Cardiology Division, Inc., St. Paul, MN (US)

(72) Inventors: Xiaoping Guo, Eden Prairie, MN (US); David P. Johnson, Brooklyn Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 876 days.

(21) Appl. No.: 14/214,548

(22) Filed: Mar. 14, 2014

(65) Prior Publication Data
US 2014/0276643 A1  Sep. 18, 2014

Related U.S. Application Data

(60) Provisional application No. 61/792,644, filed on Mar. 15, 2013.

(51) Int. Cl.
*A61M 25/00* (2006.01)
*A61M 25/01* (2006.01)
(Continued)

(52) U.S. Cl.
CPC ........... *A61L 29/126* (2013.01); *A61L 29/085* (2013.01); *A61M 25/0045* (2013.01);
(Continued)

(58) Field of Classification Search
CPC ........ A61L 29/04; A61L 29/08; A61L 29/085; A61L 29/126; A61L 29/129; A61L 2400/10; A61M 25/0012; A61M 39/10; A61M 2210/125; A61M 25/00; A61M 25/005; A61M 25/0045; A61M 25/0052–25/0054; A61M 25/0122;
(Continued)

(56) References Cited

U.S. PATENT DOCUMENTS

| 4,876,126 A | 10/1989 | Takemura et al. |
| 5,109,861 A | 5/1992 | Walinsky |

(Continued)

FOREIGN PATENT DOCUMENTS

| EP | 0558373 B1 | 10/1995 |
| EP | 0726926 B1 | 2/1998 |

(Continued)

OTHER PUBLICATIONS

Onder, S. et al. "Alteration of PTFE Surface to Increase Its Blood Compatibility", J Biomater Sci Polym Ed., Jun. 30, 2010.

*Primary Examiner* — Lee E Sanderson
(74) *Attorney, Agent, or Firm* — Dykema Gossett PLLC

(57) ABSTRACT

In various embodiments of the present disclosure, a surgical catheter is provided. The present disclosure provides a catheter shaft that includes a distal portion and a proximal portion. The proximal portion comprises a handle operably connected to the distal portion of the elongated structure. The distal portion three radially positioned polymeric layers. At least two of the layers include chemically dissimilar polymers and at least one of the three layers includes functionalized polyvinylidene fluoride (PVDF).

26 Claims, 6 Drawing Sheets

(51) Int. Cl.
*A61L 29/04* (2006.01)
*A61L 29/12* (2006.01)
*A61L 29/14* (2006.01)
*A61L 29/08* (2006.01)

(52) U.S. Cl.
CPC ...... *A61L 2400/10* (2013.01); *A61M 25/0053* (2013.01); *A61M 25/0054* (2013.01)

(58) Field of Classification Search
CPC .......... A61M 25/0147; A61M 25/0155; A61M 25/0105; A61M 25/0041; B32B 1/08
USPC .......... 604/95.01–95.05, 522–532; 428/36.9, 428/36.91, 36.9, 36.92
See application file for complete search history.

(56) References Cited

U.S. PATENT DOCUMENTS

| | | | |
|---|---|---|---|
| 5,419,374 | A | 5/1995 | Nawrot et al. |
| 5,627,079 | A | 5/1997 | Gardella |
| 5,662,622 | A | 9/1997 | Gore |
| 5,704,908 | A | 1/1998 | Hoffman et al. |
| 5,795,939 | A | 8/1998 | Lorek |
| 5,932,299 | A | 8/1999 | Kotoot |
| 5,939,492 | A | 8/1999 | Lorek |
| 6,041,826 | A | 3/2000 | Lorek et al. |
| 6,096,369 | A | 8/2000 | Anders |
| 6,143,415 | A | 11/2000 | Lorek et al. |
| 6,165,166 | A | 12/2000 | Samuelson |
| 6,500,532 | B1 | 12/2002 | Ruefer et al. |
| 6,616,982 | B2 | 9/2003 | Merrill |
| 6,911,509 | B1 | 6/2005 | Chung |
| 7,220,807 | B2 | 5/2007 | Chung |
| 7,758,892 | B1 | 7/2010 | Chen |
| 7,777,075 | B2 | 8/2010 | Ishikawa |
| 8,216,498 | B2 | 7/2012 | Quillin |
| 2002/0134451 | A1 | 9/2002 | Blasko et al. |
| 2005/0004560 | A1 | 1/2005 | Cox |
| 2005/0074570 | A1 | 4/2005 | Agrawal |
| 2005/0074605 | A1 | 4/2005 | Agrawal |
| 2005/0107870 | A1 | 5/2005 | Wang |
| 2005/0118372 | A1 | 6/2005 | Bonnet et al. |
| 2006/0083882 | A1 | 4/2006 | Schmitz |
| 2006/0198976 | A1 | 9/2006 | Trapp |
| 2007/0005024 | A1 | 1/2007 | Weber |
| 2008/0234811 | A1 | 9/2008 | Kitching |
| 2009/0131884 | A1 | 5/2009 | Yamada |
| 2009/0163851 | A1 | 6/2009 | Holloway |
| 2009/0171319 | A1* | 7/2009 | Guo ................ A61M 25/0012 604/526 |
| 2009/0188578 | A1 | 7/2009 | Bonnet et al. |
| 2009/0326647 | A1* | 12/2009 | Quillin ................ A61L 31/10 623/1.49 |
| 2010/0063476 | A1 | 3/2010 | Quilllin |
| 2010/0217235 | A1* | 8/2010 | Thorstenson ..... A61M 25/0012 604/527 |
| 2010/0228348 | A1 | 9/2010 | McClain |
| 2010/0280452 | A1 | 11/2010 | Chen et al. |
| 2012/0172840 | A1* | 7/2012 | Guo .................... A61L 29/085 604/523 |

FOREIGN PATENT DOCUMENTS

| | | |
|---|---|---|
| EP | 0696301 B1 | 12/1998 |
| EP | 0740754 B1 | 3/1999 |
| JP | 1993-095892 | 4/1993 |
| JP | 2007-000392 | 1/2007 |
| WO | 2000/059963 | 10/2000 |
| WO | 2001/017575 | 3/2001 |
| WO | 2003/066121 | 8/2003 |
| WO | 2004/000384 | 12/2003 |
| WO | 2005115496 A1 | 12/2005 |
| WO | 2006/023261 | 3/2006 |
| WO | 2007/025293 | 3/2007 |
| WO | 2007/114890 | 10/2007 |
| WO | 2009/158485 | 12/2009 |
| WO | 2012/091794 | 7/2012 |

* cited by examiner

MULTILAYERED CATHETER SHAFT CONTAINING POLYVINYLIDENE FLUORIDE POLYMERS

CROSS-REFERENCE TO RELATED APPLICATIONS

This application claims the benefit of U.S. provisional application No. 61/792,644, filed 15 Mar. 2013, which is hereby incorporated by reference as though fully set forth herein.

BACKGROUND a. Technical Field

The instant disclosure relates to catheters. In particular, the instant disclosure relates to catheter shafts which in use are guided within a human or animal so that a distal tip can be located at a remote internal location where medical equipment can be positioned or treatment fluids delivered.

b. Background Art

It is well known that catheters can be used to perform a growing number of procedures. Catheters can be used for performance of diagnostic, therapeutic, and ablative procedures, for example. Catheters include a shaft (tubular body) mounted on a handle which can guide the shaft within the vasculature system of a patient to reach a remote target site of the human anatomy where the procedure will be performed. The shaft of the catheter includes a central lumen through which one or more devices or treatment fluids can be guided to the remote target site. Such shafts need to have various physical and chemical characteristics. For instance, they need to be sufficiently flexible and durable to be reliably guided within the human anatomy or vascular system; they need to have an internal surface lubricity that facilitates the passage of other medical devices along their central lumen; they need to have a surface lubricity that allows for maneuvering the catheter within the vasculature of the patient; they should be externally hydrophobic, especially at their distal ends, to resist absorption of fluids and thus prevent shaft performance changes during medical procedures; and they should be chemically compatible with medical adhesives used to attach sensors and other monitoring devices to their outer surfaces.

The foregoing discussion is intended only to illustrate the present field and should not be taken as a disavowal of claim scope.

SUMMARY

In various embodiments, a tubular body is provided. In at least one embodiment, the tubular body can comprise three radially positioned polymeric layers. In these embodiments, at least two of the three layers can include chemically dissimilar polymers and at least one of the three layers can include functionalized polyvinylidene fluoride (PVDF).

In various embodiments, a catheter shaft is provided. In at least one embodiment, the catheter shaft can include an inner polymeric layer, a middle polymeric layer bonded to the inner polymeric layer, and an outer polymeric layer bonded to the middle polymeric layer. In these embodiments, one of the layers can include a functionalized PVDF.

In various embodiments, the catheter shaft can include a proximal segment, a transitional segment, and a distal segment. In at least one embodiment, each of the segments have an inner polymeric layer, a middle polymeric layer, and an outer polymeric layer. In various embodiments, at least one of the layers in the transitional segment can be formed of functionalized PVDF and at least one of the layers in the distal segment can be formed of functionalized PVDF.

The foregoing and other aspects, features, utilities, and advantages of the present disclosure will be apparent from reading the following description and claims, and from reviewing the accompanying drawings.

DETAILED DESCRIPTION

Figure 1:
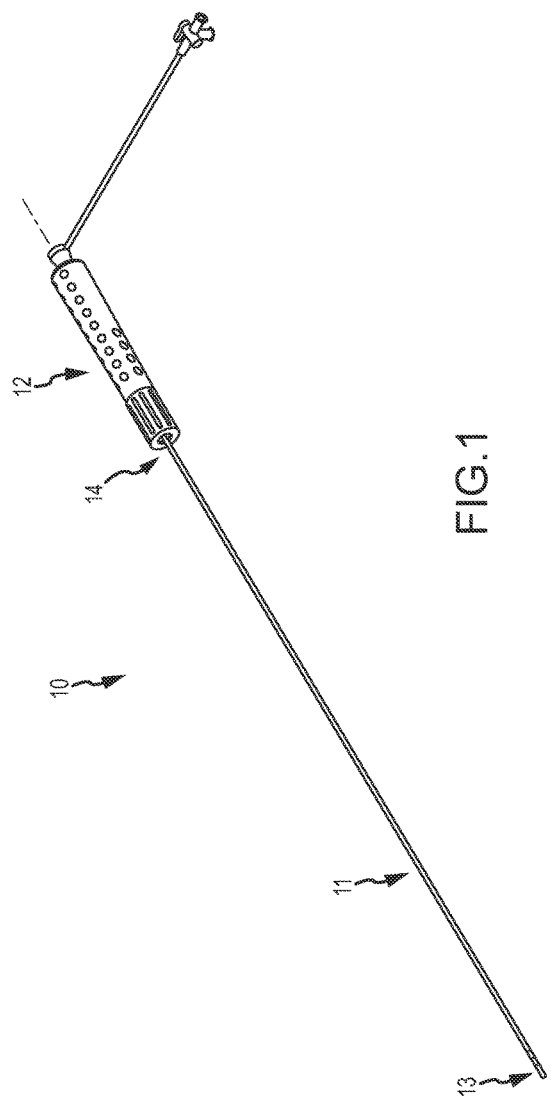
FIG. 1 is a perspective view of a catheter, according to a non-limiting embodiment.

It is well known to form catheters from multiple layers of polymeric materials which have been extruded and melt bonded together. With consideration of end-use performances of catheters, both polar and nonpolar polymers may have to be utilized. Typical polar polymers include polyamides, poly(ether block amides) copolymers (PEBA), thermoplastic polyurethanes (TPU), polyesters, poly(ester-co-ether) block polymers (PEE), etc., as these polymers display synergistically balanced mechanical properties for a catheter shaft and exhibit good chemical affinities with medical adhesives. On the other hand, nonpolar fluoropolymers such as polytetrafluoro-ethylene (PTFE), ethylene-tetrafluoroethylene-hexafluoropropylene terpolymer (EFEP), fluorinated ethylene-propylene copolymer (FEP), poly(vinylidene fluoride) (PVDF) etc., are also utilized due to their excellent surface lubricity and hydrophobicity as well as exceptional chemical resistance against body fluids. Those nonpolar fluoropolymers, in particular PTFE, are commonly used as catheter liner materials to facilitate the delivery of medical devices through the central lumens.

However, multilayered catheter shafts made of dissimilar polymers with differing chemical structures and/or molecular polarities may not have reliable layer-to-layer polymer adhesion, and layer delamination can be a risk. Tie layers which exhibit good chemical affinities with chemically dissimilar polymer layers may have to be employed. Alternatively, the bonding surfaces of the dissimilar polymeric layers may be pretreated using various physical and chemical techniques (e.g., plasma or corona treatment, chemical etching, etc.) in order to improve layer-to-layer polymer adhesions and prevent the occurrence of layer delamination. However, using tie layers or polymer surface treatment would result in increased manufacturing expenses and limit flexibility of catheter structural designs.

It is well known in the polymer industry that some selected fluoropolymers such as EFEP and PVDF can be polymerized or purposely grafted with reactive functional groups (such as amine, acrylics, carbonate, epoxides, carboxylic acids, maleic anhydride, etc.) to introduce molecular binding affinity with other polar polymers without compromising their inherent surface lubricity and chemical resistance, as required by catheter designs. Guo et al. (U.S. Appln. Pub. 2012/0172840 A1), which is incorporated herein by reference, discloses various hydrophobic catheters and compositions in which a hydrophobic and lubricious EFEP copolymer with terminal carbonate functional groups is utilized with various polar polymers such as PEBA, which is hereby incorporated by reference as though fully set forth herein. In the present disclosure, PVDF with purposely grafted reactive functional groups, such as maleic anhydride, is utilized to make various high-performance catheter shafts with synergistic consideration of not only surface lubricity and chemical resistance against body fluids, but also mechanical properties of PVDF polymers.

A reactive PVDF polymer with grafted functional groups such as maleic anhydride in place of nonpolar, nonreactive PVDF homopolymers can be used when desiring a direct bonding to an adjacent polar polymer. At the interface of bonding, the reactive functional groups of the functionalized PVDF polymer would exhibit some chemical affinity via intermolecular interactions (e.g., dispersion, dipole-dipole forces and hydrogen bonding), and even form some permanent covalent bonds with terminal and mid-chain functional groups of polar polymers, leading to a reliable polymer adhesion. In the literature, there are numerous patents and applications teaching how to use functionalized or grafted PVDF polymers to enhance the polymer adhesions between nonpolar PVDF and polar polymers primarily polyamides or nylons. U.S. Appln. Pub. 2009/0188578, which is incorporated herein by reference, discloses multilayer tubes for transferring corrosive chemical fluids which are in direct contact with a functionalized PVDF layer. Patents EP 558373, EP 696301, EP 726926 and EP 740754 disclose various multilayer tubes for petrol or gasoline. U.S. Pat. No. 8,216,498, which is incorporated herein by reference, utilizes a grafted PVDF polymer with a polar polymer to coextrude catheter shafts. However, this patent only discloses a functionalized PVDF layer directly bonded to a single adjacent polar polymer layer (bilayer), and the resultant bilayer catheter shafts may not display all the desired mechanical performances and external hydrophobicity against body fluids, which are highly desired for a versatile, high performance catheter.

FIG. 1 depicts a catheter 10 for use in connection with a number of diagnostic and therapeutic procedures performed, for example, within a human heart. For clarity and brevity purposes, the description herein will be directed primarily to a medical device, such as catheter 10, that comprises a catheter shaft, such as a tubular shaft 11, for use in cardiac applications. It will be appreciated by those having ordinary skill in the art, however, that the description below may be applicable to medical devices and apparatuses other than catheters, and for catheters, medical devices, and apparatuses used in connection with applications other than cardiac applications. Accordingly, apparatuses and medical devices other than catheters and apparatuses, medical devices, and catheters for use in applications other than cardiac applications remain within the spirit and scope of the present disclosure. As used herein, a "catheter" is defined as an elongated structure that can be inserted into and/or through a body cavity, duct, and/or vessel. Additionally, as used herein, a "catheter" means an elongated structure that can be inserted into and/or through a body cavity, duct, and/or vessel. Accordingly, the catheter can be sized and configured to be inserted into a patient's body. In at least one embodiment, a catheter may be hollow and/or define a lumen therethrough for passing another medical device, such as a guidewire or another catheter, for example. However, in various embodiments, a catheter may be closed at least at its distal end.

As illustrated in FIG. 1, a catheter 10 includes a tubular shaft 11 and a handle 12. The shaft 11 can be configured to be at least partially inserted into and/or through a body passage or another anatomic structure, such as a human patient's vasculature, including a blood vessel. The handle 12 can include an internal manipulation mechanism (not shown) for manipulating a distal tip 13 of the shaft 11. The shaft 11 can be mounted at its proximal end 13 in the handle 12 such that manual manipulation of the handle 12 via the internal manipulation mechanism will direct the movement of the shaft 11 and/or distal tip 13 inside a person of interest. The shaft 11 is formed of either melt- or adhesive-bonded polymeric layers which are radially positioned relative to one another, and which define a central lumen for the passage of the internal manipulation device or other medical devices (not shown) or the flow of treatment liquids to the distal tip 13 of the shaft 11 that is in contact with the anatomical target being inspected or treated.

Figure 2:
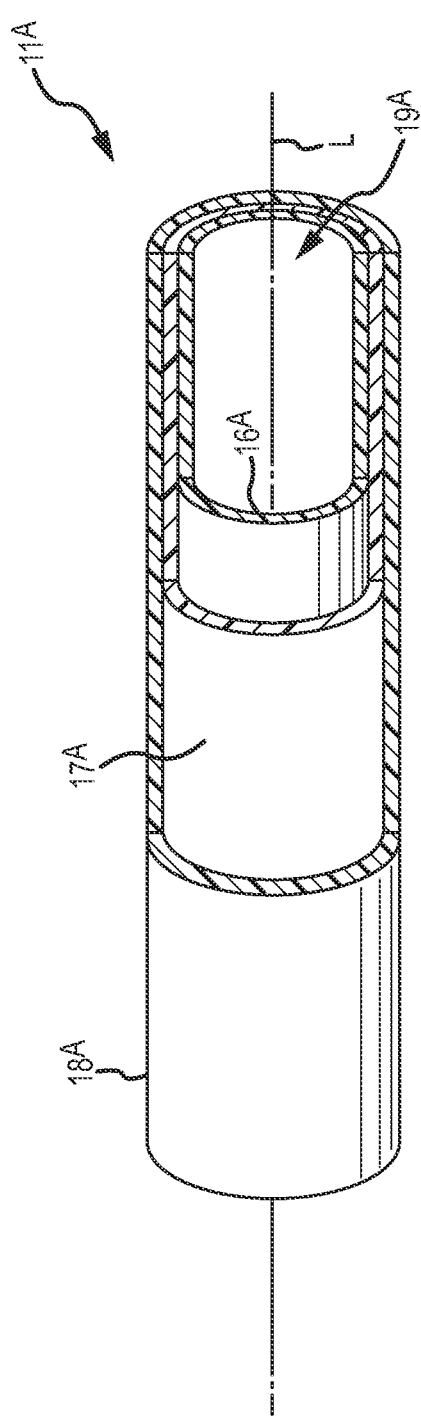
FIG. 2 is an isometric view of a section of a catheter shaft according to a first non-limiting embodiment.

FIG. 2 depicts an isometric view of a section of a catheter shaft $11^A$ according to a first non-limiting embodiment. In some embodiments, the shaft $11^A$ can include three radially positioned polymeric layers that define a lumen $19^A$. For example, the shaft $11^A$ can include an inner polymeric layer $16^A$, a middle polymeric layer $17^A$, and an outer polymeric layer $18^A$. The middle polymeric layer $17^A$ can be bonded to the inner polymeric layer $16^A$ and the outer polymeric layer $18^A$ can be bonded to the middle polymeric layer $17^A$. At least two of the three polymeric layers can include chemically dissimilar polymers and at least one of the three polymeric layers can include a functionalized polyvinylidene fluoride (PVDF). In addition to the functionalized PVDF, the polymers making up the at least two of the three polymeric layers can be chosen from polar polymers, PVDF homopolymers, and PVDF copolymers.

The functionalized PVDF can be a PVDF homopolymer or copolymer grafted with at least one functional monomer having at least one functional group such as a carboxylic acid, carboxylic acid salt, carbonate, carboxylic acid anhydride, epoxide, carboxylic acid ester, carboxylic amide, silyl, alkoxysilane, hydroxyl, and isocyanate. Preferably, the functionalized PVDF is grafted with at least one functional monomer having at least one functional group such as maleic anhydride (commercially available from Arkema, Inc. under the trademark KYNAR ADX®) and/or glycidyl methacrylate. PVDF homopolymers include repeating units of vinylidene fluoride (VDF) monomer. They are commercially available from multiple commercial resources, including KYNAR® (Arkema Inc.), Dyneon™ PVDF homopolymers (3M Dyneon Company), Solef® PVDF homopolymers (Solvay), Hylar® (Solvay), Dyflor® (Evonic Industries) etc. Preferably, the functionalized PVDF includes a PVDF homopolymer grafted with maleic anhydride.

According to various embodiments, PVDF copolymers may be obtained by polymerizing VDF monomer with one or two other co-monomers such as hexafluoropropylene (HFP), mono-fluoroethylene, trifluoroethylene and tetrafluoroethylene. PVDF copolymers are commercially available from multiple commercial resources, including Dyneon™ PVDF copolymers (3M Dyneon Company) Solef® PVDF copolymers (Solvay Specialty Polymers), etc. The preferred PVDF copolymers (and used in the examples) were copolymers of VDF and HFP, which are commercially available from Arkema, Inc. under the trademark (KYNAR FLEX®). In some embodiments the PVDF copolymer can be a functionalized PVDF copolymer, including a copolymer of VDF and HFP grafted with maleic anhydride.

Polar polymers are polymers having a polymer chain containing polar atoms such as oxygen, nitrogen, halogen atoms and sulfur, or polar groups that likely exhibit-attractive intermolecular forces (e.g., dipole-dipole forces, hydrogen bonding, etc.) to itself and other dissimilar polymers. In general, a polar polymer has a much higher surface energy than a typical nonpolar polymer like polypropylene or PVDF homopolymer. Typical polar polymers include polyamides (e.g. nylon 11, nylon 12, nylon 612, nylon 66, nylon 6, etc.), engineering thermoplastic polyurethanes, polyesters (e.g., poly(ethylene terephthalate), poly(butylene terephthalate)), polyester-based thermoplastic elastomers, polyamide-based thermoplastic elastomers, thermoplastic polyurethane elastomers, polycarbonate, functionalized polyolefins, poly (ether block amide) copolymers, etc.

PVDF homopolymers and copolymers are melt-processable fluoroplastics, making the polymers suitable for use in forming the shaft $11^A$ because of their ability to be processed. In addition, as discussed herein, PVDF polymers offer a surface lubricity and hydrophobicity that can increase a performance of the shaft $11^A$. Increased surface lubricity of the materials that form an inner surface of the shaft $11^A$ that defines a guidewire lumen can facilitate movement of the guidewire therein by reducing aggregation of fibrin and plasma proteins. Additionally, increased surface lubricity of the materials that form an outer surface of the shaft $11^A$ can reduce organ damage as the shaft $11^A$ is passed through the patient's vasculature as well as pain felt by a patient. Increased hydrophobicity of the materials that form the inner surface and/or outer surface can aid in reducing absorption of fluids being passed through the lumen and/or contacting the outer surface of the shaft $11^A$.

As discussed herein, nonpolar polymers can offer desirable mechanical properties, as well as affinities for medical adhesives. As such, the layered shaft $11^A$ that includes a composite of nonpolar and/or polar materials in various layers can have balanced mechanical properties, as well as a desirable surface lubricity and hydrophobicity.

However, polar polymers such as PVDF homopolymers and PVDF copolymers can have poor adhesion to chemically dissimilar polymers. Accordingly, various embodiments of the present disclosure can increase adhesion between the chemically dissimilar polymers by including a functionalized PVDF layer in at least one of the three layers of the shaft $11^A$.

In some embodiments, the middle polymeric layer $17^A$ can be formed of functionalized PVDF and the inner polymeric layer $16^A$ and the outer polymeric layer $18^A$ can be chemically dissimilar polymers to one another. For example, the inner polymeric layer $16^A$ can be a polar polymer (e.g., polyamide) and the outer polymeric layer $18^A$ can be a nonpolar polymer (e.g., PVDF copolymer, PVDF homopolymer). Alternatively, the inner polymeric layer $16^A$ can be a non-polar polymer and the outer polymeric layer $18^A$ can be a polar polymer. Because the functionalized PVDF has a reactive functional group, the chemically dissimilar polymers forming the inner polymeric layer $16^A$ and the outer polymeric layer $18^A$ can be bonded together by the middle polymeric layer $17^A$ of functionalized PVDF.

Alternatively, the middle polymeric layer $17^A$ can be a functionalized PVDF polymer and the inner polymeric layer $16^A$ and the outer polymeric layer $18^A$ can be chemically similar polymers bonded to the middle polymeric layer $17^A$ of functionalized PVDF polymer. In some examples, the inner polymeric layer $16^A$ and the outer polymeric layer $18^A$ can be nonpolar polymers, which can provide a shaft $11^A$ that is flexible and has a desired hydrophobicity and lubricity within the ranges specified herein. For instance, the inner polymeric layer $16^A$ and the outer polymeric layer $18^A$ can be PVDF copolymers; the inner polymeric layer $16^A$ and the outer polymeric layer $18^A$ can be PVDF homopolymers; the inner polymeric layer $16^A$ can be a PVDF homopolymer and the outer polymeric layer $18^A$ can be a PVDF copolymer; or the inner polymeric layer $16^A$ can be a PVDF copolymer and the outer polymeric layer $18^A$ can be a PVDF homopolymer.

In some embodiments, the functionalized PVDF can be used to form the inner polymeric layer $16^A$ and/or the outer polymeric layer $18^A$. Forming the inner polymeric layer $16^A$ and/or the outer polymeric layer $18^A$ with the functionalized PVDF can facilitate bonding of subassemblies to the inner polymeric layer $16^A$ and/or the outer polymeric layer $18^A$. For instance, in reference to FIG. 1, a tip (e.g., electrode tip) can be bonded to the distal tip 13 of the shaft 11. Bonding to the inner polymeric layer $16^A$ and/or the outer polymeric layer $18^A$ can be performed with a UV curing epoxy, such as a diacrylate adhesive. In some examples, the inner polymeric layer $16^A$ and the outer polymeric layer $18^A$ can be formed from PVDF and the middle polymeric layer $17^A$ can be formed from a polar polymer (e.g., nylon). As such, while subassemblies can be bonded to the inner polymeric layer $16^A$ and/or outer polymeric layer $18^A$ of functionalized PVDF, the middle polymeric layer $17^A$ of polar polymer can also provide the shaft $11^A$ with desired mechanical properties.

In some embodiments, when the inner polymeric layer $16^A$ is made from functionalized PVDF, the middle polymeric layer $17^A$ and/or the outer polymeric layer $18^A$ can be formed from a PVDF copolymer and/or a PVDF homopolymer, in some examples. Alternatively, when the outer polymeric layer $18^A$ is formed from functionalized PVDF, the middle polymeric layer $17^A$ and/or the inner polymeric layer $16^A$ can be made from a PVDF copolymer and/or a PVDF homopolymer, in some examples.

In some embodiments, when the inner polymeric layer $16^A$ is made from functionalized PVDF, the middle polymeric layer $17^A$ and/or the outer polymeric layer $18^A$ can be formed from polar polymers, in some examples. Alternatively, when the outer polymeric layer $18^A$ is formed from functionalized PVDF, the middle polymeric layer $17^A$ and/or the inner polymeric layer $16^A$ can be made from polar polymers, in some examples.

Figure 3:
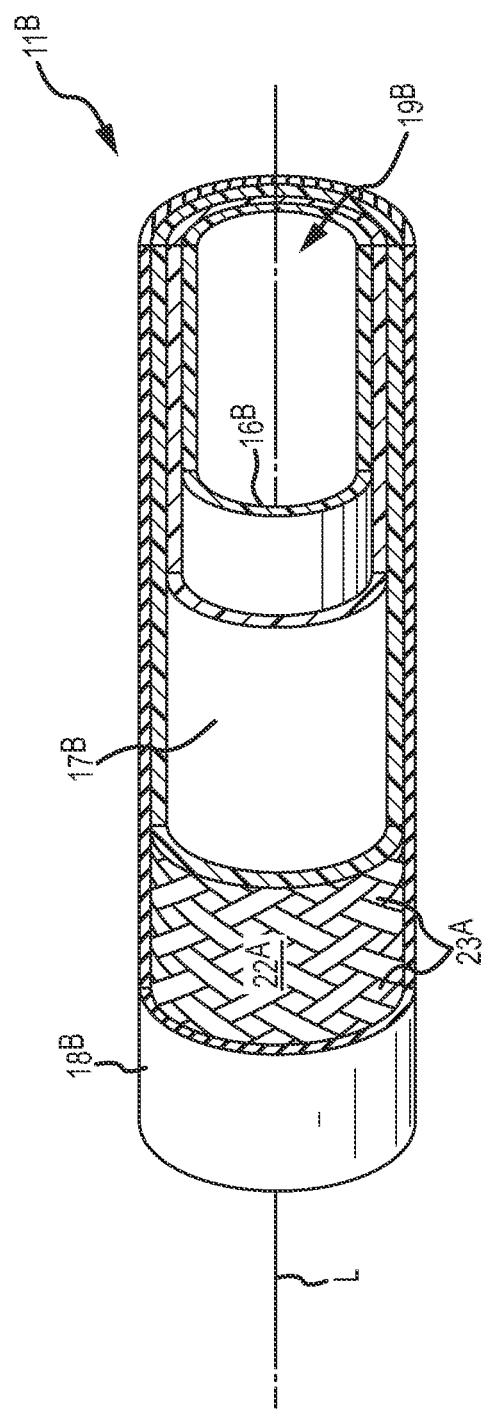
FIG. 3 is an isometric view of a section of a catheter shaft according to a second non-limiting embodiment.

FIG. 3 depicts an isometric view of a section of a catheter shaft $11^B$ according to a second non-limiting embodiment. The shaft $11^B$ includes an inner polymeric layer $16^B$, middle polymeric layer $17^B$, and outer polymeric layer $18^B$ that define a lumen $19^B$. The inner polymeric layer $16^B$, the middle polymeric layer $17^B$, and the outer polymeric layer $18^B$ can be formed from the same combination of polymers as discussed in relation to shaft $11^A$, in FIG. 2. In addition, a metal wire braid layer $22^A$ can be embedded at or near (e.g., proximate to) an interface of the middle polymeric layer $17^B$ and outer polymeric layer $18^B$. In some embodiments, the metal wire braid layer $22^A$ can provide additional hoop strength to the shaft $11^B$, while still permitting the shaft $11^B$ to be flexible and/or compliant. The additional hoop strength can result in an increased kink resistance of the shaft $11^B$.

Owing to a braid pattern of the metal wire braid layer $22^A$, openings $23^A$ may be defined within the metal wire braid layer $22^A$. The outer polymeric layer $18^B$ and the middle polymeric layer $17^B$ can, in some instances, bind with one another through the openings $23^A$. As such, the outer polymeric layer $18^B$ and the inner polymeric layer $17^B$ can form a cohesive bond with one another, even though the metal wire braid layer $22^A$ is located at an interface of the two layers.

Alternatively, the metal wire braid layer $22^A$ can be wholly and/or partly contained within the outer polymeric layer $18^B$ and/or the middle polymeric layer $17^B$. In some embodiments, it may be desirable to contain the metal wire braid layer $22^A$ wholly within the middle polymeric layer $17^B$. Containing the metal wire braid layer $22^A$ wholly within the middle polymeric layer $17^B$ can prevent wires associated with the metal wire braid layer $22^A$ from protruding from the inner polymeric layer $17^B$ and/or outer polymeric layer $18^B$.

Figure 4:
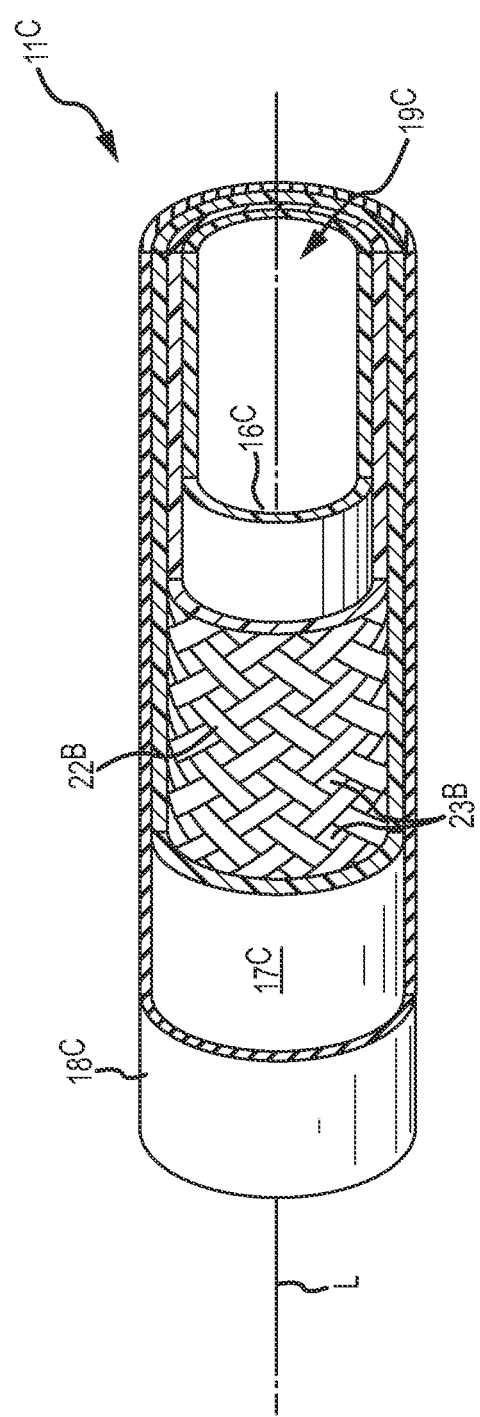
FIG. 4 is an isometric view of a section of a catheter shaft according to a third non-limiting embodiment.

FIG. 4 depicts an isometric view of a section of a shaft $11^C$ according to a third non-limiting embodiment. The shaft $11^C$ includes an inner polymeric layer $16^C$, middle polymeric layer $17^C$, and outer polymeric layer $18^C$ that define a lumen $19^C$. The inner polymeric layer $16^C$, the middle polymeric layer $17^C$, and the outer polymeric layer $18^C$ can be formed from the same combination of polymers as discussed in relation to shaft $11^A$, in FIG. 2. A metal wire braid layer $22^B$ can be embedded at or near an interface of the inner polymeric layer $16^C$ and the middle polymeric layer $17^C$. As discussed in relation to FIG. 3, the metal wire braid layer $22^B$ can provide additional hoop strength to the shaft $11^C$, while still permitting the shaft $11^C$ to be flexible and/or compliant. Additionally, as discussed in relation to FIG. 3, the metal wire braid layer $22^B$ can be located at an interface of the two layers and/or can be wholly contained within the middle polymeric layer $17^C$ to prevent protrusion of wires associated with the metal braid layer $22^B$.

In some embodiments, a polymeric layer adjacent to the metal wire braid layer, for example the inner polymeric layer $16^C$ and middle polymeric layer $17^C$ in FIG. 4 and the outer polymeric layer $18^B$ and middle polymeric layer $17^B$ in FIG. 3 can form a bond with the metal wire braid layer when the adjacent polymeric layer is formed of functionalized PVDF. In an example, the functionalized PVDF can have a reactive functional group that can bond with metal. As such, the polymeric layer that is adjacent to the metal wire braid layer $22^B$ and/or contains the metal wire braid layer $22^B$ can be formed of functionalized PVDF, according to some embodiments of the present disclosure. Forming the polymeric layer adjacent to the metal wire braid layer $22^B$ and/or a polymeric layer that contains the metal wire braid layer $22^B$ out of functionalized PVDF can reduce a chance of the shaft delaminating. For example, since the reactive functional group of the functionalized PVDF can bond to the metal, a reduced chance of delamination may be present as opposed to when other types of polymers (e.g., polyamides) are located adjacent to and/or contain the metal wire braid layer $22^B$.

In other embodiments (not specifically depicted) the catheter shaft $11^C$ can include metal wire braid layers between both the inner polymeric layer $16^C$ and middle polymeric layer $17^C$ and between the middle polymeric layer $17^C$ and outer polymeric layer $18^C$. Alternatively, the metal wire braid layers can be omitted, for example, in FIG. 2.

As discussed herein, in an embodiment, at least one of the inner polymeric layer $16^C$, middle polymeric layer $17^C$, and outer polymeric layer $18^C$ is composed of functionalized PVDF and at least two of the layers are composed of chemically dissimilar polymers. In an example, the functionalized PVDF can enable bonding between layers, bonding of a subassembly to an outer and/or inner layer, and/or bonding of a metal wire braid layer.

Figure 5:
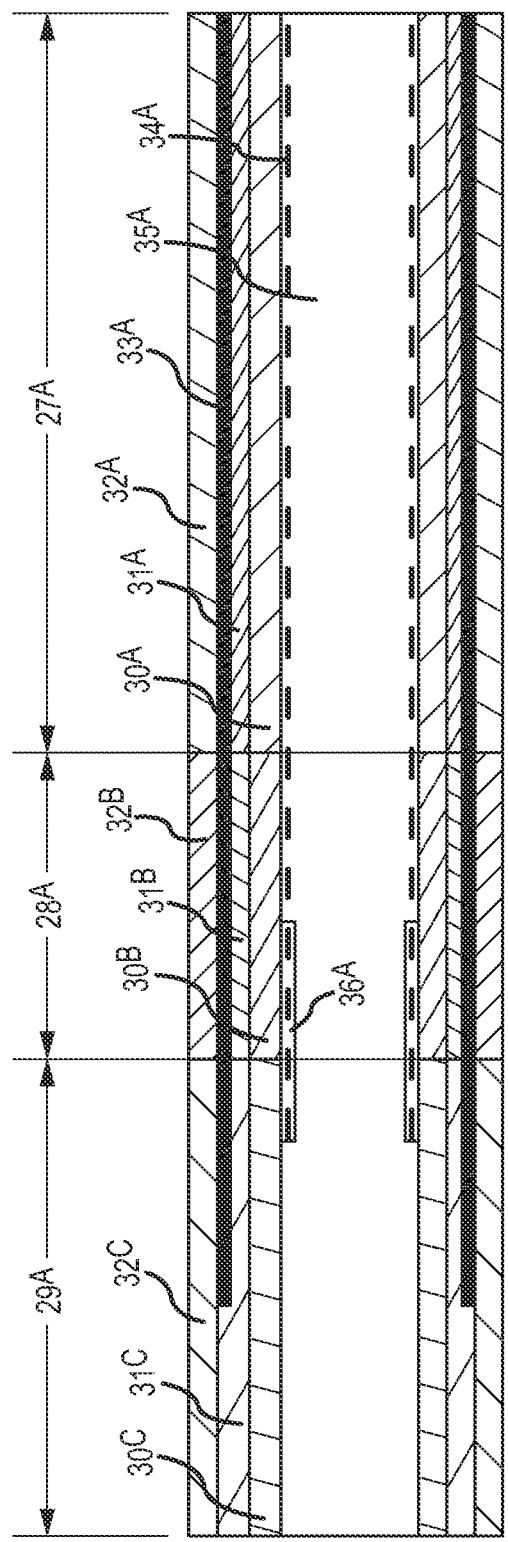
FIG. 5 is a partial cross-sectional view of a section of a catheter shaft according to a fourth non-limiting embodiment.

FIG. 5 depicts a partial cross-sectional view of a section of a shaft $26^A$ according to a fourth non-limiting embodiment. The shaft $26^A$ includes a proximal segment $27^A$, a transitional segment $28^A$, and a distal segment $29^A$. In some embodiments, each of the segments $27^A$, $28^A$, $29^A$ have an inner polymeric layer $30^A$, $30^B$, $30^C$ a middle polymeric layer $31^A$, $31^B$, $31^C$, and an outer polymeric layer $32^A$, $32^B$, $32^C$, respectively.

As discussed herein, it can be desirable to have different mechanical properties for different segments $27^A$, $28^A$, $29^A$ of the shaft $26^A$. For example, it can be desirable to have a proximal segment $27^A$ with a high column strength to effectively transfer a manipulating force placed on the catheter handle (e.g., proximal segment) by a physician. In addition, it can be desirable to have a distal segment $29^A$ with a good mechanical flexibility or deflectability, high surface lubricity, and hydrophobicity, etc. Accordingly, some embodiments of the present disclosure can provide for a shaft $26^A$ having segments with varying mechanical properties.

In some embodiments, the inner polymeric layer $30^A$, $30^B$, $30^C$ the middle polymeric layer $31^A$, $31^B$, $31^C$, and/or the outer polymeric layer $32^A$, $32^B$, $32^C$ can be formed from the same polymer. For example, the proximal segment $27^A$, transitional segment $28^A$, and/or the distal segment $29^A$ of the middle polymeric layer $30^A$, $30^B$, $30^C$ can be formed from the same polymer, giving the middle polymeric layer $30^A$, $30^B$, $30^C$ uniform mechanical characteristics along a length of the shaft $26^A$. Alternatively, the proximal segment $27^A$, transitional segment $28^A$, and/or distal segment $29^A$ of the middle polymeric layer $30^A$, $30^B$, $30^C$ can be made from different polymers, giving the middle polymeric layer $30^A$, $30^B$, $30^C$ varying mechanical characteristics along a length of the shaft $26^A$.

In some examples, by forming the middle polymeric layer $30^A$, $30^B$, $30^C$ from different polymers (e.g., polymers with different flexibilities), a flexibility of the middle polymeric layer $30^A$, $30^B$, $30^C$ can increase from the proximal segment $27^A$ to the distal segment $29^A$. As such, a maneuverability of the distal segment $29^A$ can be increased, which can be beneficial when feeding the distal segment through vasculature of a patient to a position where a medical procedure is to be performed with the shaft $26^A$.

In some embodiments, the inner polymeric layer $30^A$, middle polymeric layer $31^A$, and outer polymeric layer $32^A$ of the proximal segment $27^A$ can be formed from at least one type of polar polymer (e.g., polyamide). Forming each of the layers of the proximal segment $27^A$ from the polar polymer can provide a high column strength to effectively transfer a manipulating force placed on the catheter handle, while at the same time reducing a materials cost associated with construction of the proximal segment $27^A$.

In some embodiments, the inner polymeric layers $30^B$, $30^C$ of the transitional segment $28^A$ and the distal segment $29^A$ can be formed from the at least one type of polymer. In an example, the inner polymeric layers $30^B$, $30^C$ can be made of the same type of polar polymer that forms the proximal segment. As such, the inner polymeric layers $30^A$, $30^B$, $30^C$ can be formed of one continuous polar polymeric layer.

In embodiments where the inner polymeric layer $30^A$, middle polymeric layer $31^A$, and outer polymeric layer $32^A$ of the proximal segment $27^A$ are formed from at least one type of polar polymer, a bond between the proximal segment $27^A$ and the transitional segment $28^A$ may not be obtained when layers of the transitional segment $28^A$ are chemically dissimilar to corresponding layers of the proximal segment $27^A$ (e.g., polar and non-polar polymers). As such, embodiments of the present disclosure can include a tie band, which can bond chemically dissimilar layers of the proximal segment and transitional segment, as discussed further in relation to FIG. 6.

In some embodiments, the inner polymeric layers $30^A$, $30^B$, $30^C$ and/or outer polymeric layers $32^A$, $32^B$, $32^C$ can be formed from functionalized PVDF. The functionalized PVDF can act as a hydrophobic barrier layer. During clinical procedures, catheter shafts may be exposed to aqueous surroundings of the vessel and human anatomy for a prolonged time, and any exposed polar polymeric materials of a catheter shaft may, as a consequence, unavoidably absorb water, which may act as a plasticizer for exposed polar polymeric shafts. Tests have shown that PEBA based catheters, for example, that do not include a hydrophobic barrier layer, may absorb water at an amount of up to 2% by weight upon immersion into saline. The moisture absorbed into the materials may act as a plasticizer, potentially leading to decreases in the catheter shaft's mechanical strength and stiffness/rigidity. As a result, such shafts could exhibit mechanical softening phenomena over time, which could lead to decreases in mechanical strength, column stiffness, pushability, torqueability, and the like. As a consequence, this softening could lead to changes in end-use performance, such as compromised catheter shaft deliverability along a vessel and poor shaft maneuverability within the target human anatomy. Moreover, any such in-procedure performance changes could affect an operating physician's perception of use.

The hydrophobic barrier layer described above may be useful to prevent or resist water or any aqueous medium from being absorbed by the catheter shaft. As noted above, typically, catheter shafts are made of polar polymeric materials and providing a hydrophobic barrier layer may prevent the degradation of mechanical properties that may occur where the polar polymeric materials would have previously been exposed to an aqueous environment and absorb water and/or other fluids. Therefore, providing a hydrophobic barrier layer to the exterior of a catheter shaft may help minimize or eliminate the changes in shaft deliverability and/or maneuverability during a surgical procedure. Also, providing a hydrophobic barrier layer to the interior of a catheter shaft may help minimize or eliminate the changes in shaft deliverability and/or maneuverability due to saline from an irrigation lumen, either a central lumen or one or more such lumens in the wall of a catheter, for example.

Some embodiments of the present disclosure can include a metal wire braid layer $33^A$, as discussed in relation to FIGS. 3 and 4. For example, the metal wire braid layer $33^A$ can be embedded proximate to an interface of the middle polymeric layers $31^A$, $31^B$, $31^C$ and the outer polymeric layers $32^A$, $32^B$, $32^C$, as shown in FIG. 4, and/or the metal wire braid layer $33^A$ can be embedded proximate to an interface of the middle polymeric layers $31^A$, $31^B$, $31^C$ and the inner polymeric layers $30^A$, $30^B$, $30^C$. As discussed herein, the metal wire braid layer $33^A$ can provide an increased kink resistance to the shaft $26^A$.

In some embodiments, the shaft $26^A$ can include a reinforcing spring $34^A$ that extends along the inner polymeric layers $30^A$, $30^B$, $30^C$ of the shaft $26^A$. The reinforcing spring $34^A$ can be located within the lumen $35^A$ of the shaft $26^A$ and can extend from the proximal segment $27^A$ to a portion of the distal segment $29^A$. For example, the spring may partially extend through the distal segment $29^A$ so as to maintain a maneuverability and flexibility of the distal segment $29^A$. In addition, partially extending the distal segment $29^A$ through the distal segment aids in torque transfer between the proximal segment $27^A$ and the distal segment $29^A$, while increasing a kink resistance of the shaft $26^A$ along a length of the reinforcing spring $34^A$.

A protective shrink tube $36^A$ can be placed around a distal end of the reinforcing spring $34^A$, which can contain the distal end of the reinforcing spring $34^A$. The protective shrink tube $36^A$ can be made from functionalized PVDF, which can be bonded to the inner polymeric layer $30^B$ of the transitional segment $28^A$ and/or the inner polymeric layer $30^C$ of the distal segment $29^A$. In some embodiments, the protective shrink tube $36^A$ can be placed around the distal end of the reinforcing spring $34^A$ to alleviate a stress rise that can be caused by sudden changes in the internal structure of the shaft $26^A$.

Figure 6:
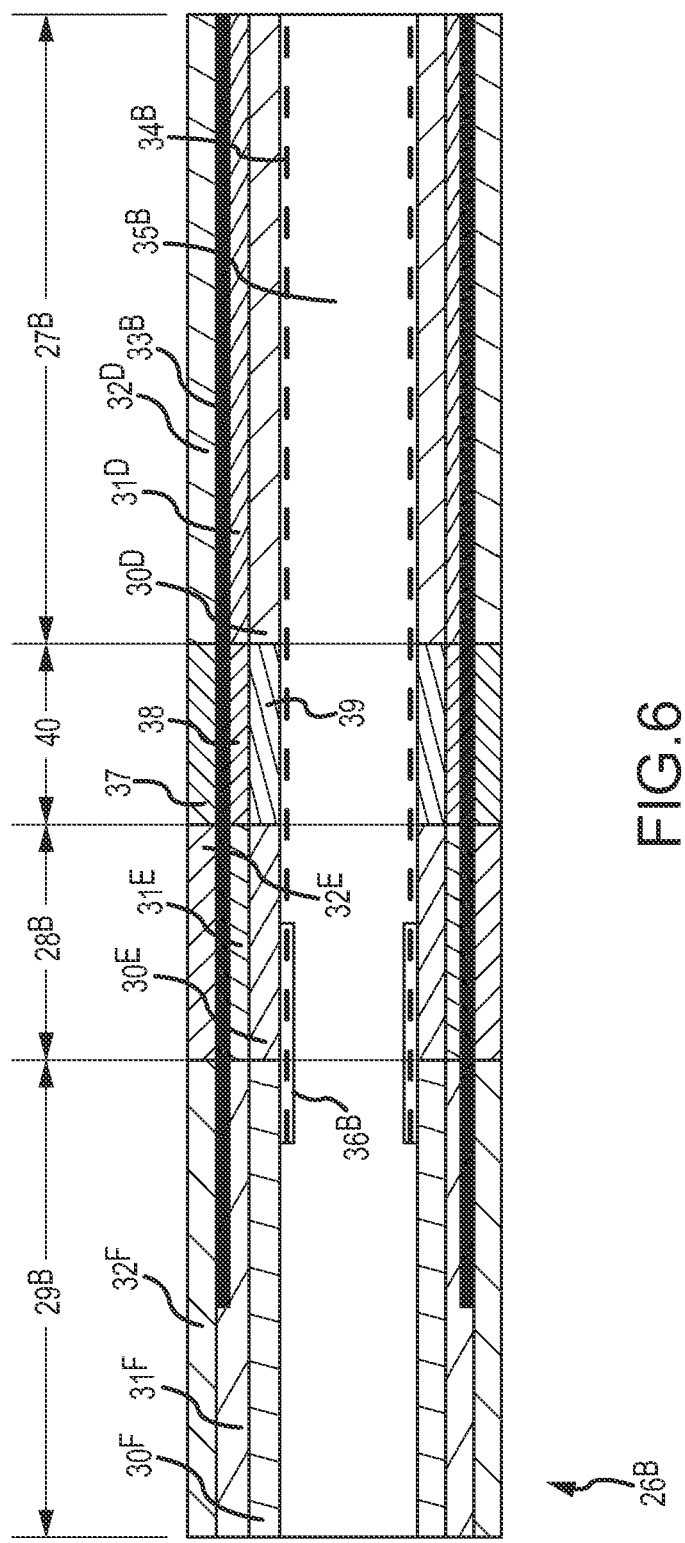
FIG. 6 is a partial cross-sectional view of a section of a catheter shaft according to a fifth non-limiting embodiment.

FIG. 6 depicts a partial cross-sectional view of a section of a shaft $26^B$ according to a fifth non-limiting embodiment. The shaft $26^B$ includes a proximal segment $27^B$, tie band 40, transitional segment $28^B$, and distal segment $29^B$. The shaft includes inner polymeric layers $30^D$, 39, $30^E$, $30^F$, middle polymeric layers $31^D$, 38, $31^E$, $31^F$, and outer polymeric layers $32^D$, 37, $32^E$, $32^F$. Additionally, the shaft can include the metal wire braid layer $33^B$, the reinforcing spring $34^B$, and shrink tube $36^B$.

As discussed herein, when a particular polymeric layer of the proximal segment $27^B$ is chemically dissimilar from a corresponding polymeric layer of the transitional segment $28^B$, a bond may not be obtained between the polymeric layers. As such, embodiments of the present disclosure can include a tie band 40 that consists of an outer polymeric layer 37, middle polymeric layer 38, and/or inner polymeric layer 39 of functionalized PVDF, depending on which corresponding polymeric layers of the transitional segment $28^B$ and the proximal segment $27^B$ are chemically dissimilar.

In some embodiments, a high hydrophobicity can be provided only for the deflectable distal segment $29^B$ and transitional segment $28^B$, while the lengthy proximal segment $27^B$ of the catheter shaft $26^B$ can be made of relatively economical polymeric materials like polyamide-based thermoplastic elastomers, thermoplastic polyurethanes, thermoplastic polyester-based elastomers, polyesters, and polyamides, etc.

In one embodiment, the inner polymeric layers $30^D$, 39, $30^E$, $30^F$ can be selected from polar polymeric materials such as polyamide-based thermoplastic elastomers, thermoplastic polyurethanes, thermoplastic polyester-based elastomers, polyamides, and can extend the whole length of the catheter shaft $26^B$. The middle polymeric layer $31^D$ and outer polymeric layer $32^D$ for the proximal segment $27^B$ of the catheter shaft $26^B$ can be formed from a same polymer as the inner polymeric layer $30^D$, or can be formed from a polymer selected from the same family as the inner polymeric layer $30^D$ with higher or lower durometer.

Between the proximal segment $27^B$ and transition segment $28^B$ of the shaft, the functionalized PVDF tie band 40 can be overlaid on the polar, inner polymeric layer 39. The middle polymeric layer 38 of the tie band 40 can be formed from functionalized PVDF and can extend from the transitional segment $28^B$ to the deflectable distal segment $29^B$. In some embodiments, the outer polymer layer 37 of the tie band 40 can be formed of functionalized PVDF, while the outer polymeric layers $32^E$ and $32^F$ can be selected from PVDF homopolymers or copolymers having different durometers or mechanical flexibilities (such as KYNAR FLEX® 2750 and KYNAR FLEX® 2500) for the transitional segment $28^B$ and distal segment $29^B$ of the shaft $26^B$, respectively. This can result in the distal segment $29^B$ having an increased flexibility over the transitional segment $28^B$.

The metal wire braid layer $33^B$ can extend from the proximal segment $27^B$ to the transitional segment $28^B$ or a portion of the deflectable distal segment $29^B$.

In this embodiment, the functionalized PVDF tie band 40 can provide good face-to-face, axial polymer adhesions between the polar, proximal segment $27^B$ and the hydrophobic, transitional segment $28^B$ (or the deflectable distal segment $29^B$) of the catheter shaft $26^B$. In addition, the PVDF tie band 40 also acts as a hydrophobic shut-off barrier dividing the catheter shaft $26^B$ into two portions: the hygroscopic (or polar), proximal portion $27^B$ and the hydrophobic (or nonpolar), portion (e.g., tie band 40, transitional segment $28^B$ and distal segment $29^B$). Moreover, within the transitional segment $28^B$ and distal segment $29^B$, the functionalized PVDF middle polymeric layers $31^E$, $31^F$ enable sound layer-to-layer adhesions between polar inner polymeric layers $30^E$, $30^F$, metal wire braid layer $33^B$ and nonpolar hydrophobic outer polymeric layers $32^E$, $32^F$.

Examples of the inner, middle and outer polymeric layers of at least portions (or segments) of a catheter shaft according to plural embodiments are as follows.

Example 1

All Layers Include PVDF Homopolymers and Copolymers

A multilayered catheter shaft included an inner polymeric layer of PVDF homopolymer (KYNAR® 460), a middle polymeric layer of PVDF copolymer (KYNAR FLEX® 3120), and an outer polymeric layer of functionalized PVDF (KYNAR ADX®). The shaft exhibited good flexibility, balanced mechanical strengths, excellent internal and external surface lubricity, and high chemical resistance against body fluids or medical agents. Relatively, the outer polymeric layer of functionalized PVDF and inner polymeric layer of PVDF homopolymer provided layers with lubricities greater than that associated with a polar polymer, such as nylon. Due to the outer polymeric layer being made of functionalized PVDF, subassemblies with other functional components could be attached to the shaft using adhesive bonding techniques. If an increased kink resistance is desired, a metal wire braid layer could be included between the outer and middle polymeric layers to provide enhanced shaft strength and kink resistance.

Example 2

All Layers Include PVDF Homopolymers and Copolymers

A multilayered catheter shaft included an inner polymeric layer of PVDF homopolymer (KYNAR® 460), a middle polymeric layer of functionalized PVDF (KYNAR ADX®), and an outer polymeric layer of PVDF homopolymer (KNAR® 460). The shaft displayed excellent internal and external surface lubricity and chemical resistance against body fluids and medical fluids if applicable. Relatively, the inner and outer polymeric layers of PVDF homopolymer provided layers with lubricities greater than that associated with a polar polymer, such as nylon. When a metal wire braid layer was included between inner and middle polymeric layers or between the middle and outer polymeric layers, the shaft displayed enhanced shaft strength and excellent kink resistance.

Example 3

All Layers Include PVDF Homopolymers and Copolymers

A multilayered catheter shaft including an inner polymeric layer of PVDF copolymer (KYNAR FLEX® 2500), a middle polymeric layer of functionalized PVDF (KYNAR ADX®), and an outer polymeric layer of PVDF copolymer (KYNAR FLEX® 2750). The shaft was highly flexible, but displayed excellent surface lubricity and high chemical resistances against body fluids or medical agents. Relatively, the inner and outer polymeric layers of PVDF homopolymer provided layers with lubricities greater than that associated with a polar polymer, such as nylon.

Example 4

Functionalized PVDF Inner and Outer Polymeric Layers with Metal Wire Braid Layer A multilayered catheter shaft included an inner polymeric layer of functionalized PVDF (KYNAR ADX®), a middle polymer layer of nylon 12 (Rilsan AESNO or Pebax 7233/7033), and an outer polymeric layer of functionalized PVDF (KYNAR ADX®). A metal wire braid was included between the inner and middle polymeric layers, or between the middle and outer polymeric layers. It should be noted that some polar polymers contain reactive functional groups as their terminal groups (amido, epoxy, hydroxyl, isocyanate, and urethane, etc.) and thus can adhere to functionalized PVDF (copolymer) grafted with maleic anhydride monomers, when they are melt coextruded. Polar polymers provide a wide spectrum of mechanical performance characteristics in catheter shafts, while the PVDF polymers provide excellent water resistance and surface lubricity. The outer functionalized PVDF layer enabled adhesive bonding thereto of typical subassemblies, whereas the inner functionalized PVDF layer provided excellent surface lubricity for the central lumens of the shaft. Relatively, the inner and outer polymeric layers of functionalized PVDF provided layers with lubricities greater than that associated with a polar polymer, such as nylon.

Example 5

Functionalized PVDF Middle Polymeric Layer and PVDF Copolymer Outer Polymeric Layer with Metal Wire Braid Layer A multilayered catheter shaft included an inner polymer layer of nylon 12 (Rilsan AESNO P40TL or Pebax 4033/3533), a middle polymeric layer of functionalized PVDF (KYNAR ADX®), and an outer polymeric layer of PVDF copolymer (KNAR FLEX® 2750). A metal wire braid layer was optionally included between the inner and middle polymeric layers or between the middle and outer polymer layers. The outer layer of PVDF copolymer provided high moisture resistance and excellent surface lubricity, the inner layer of polar polymer provided good mechanical properties, and the middle layer of functionalized PVDF acted as a tie or adhesive layer integrating the inner and outer layers, which were chemically very dissimilar. Relatively, the outer polymeric layer of PVDF copolymer provided a layer with a lubricity greater than that associated with a polar polymer, such as nylon. The metal wire braid layers, when used between the inner and middle layers or between the outer and middle layers, provided enhanced kink resistance and shaft strength.

Example 6

Functionalized PVDF Middle Polymeric Layer and PVDF Homopolymer Inner Polymeric Layer with Metal Wire Braid Layer A multilayered catheter shaft included an inner polymeric layer of PVDF homopolymer (KYNAR® 460), a middle polymeric layer of functionalized PVDF (KYNAR ADX®), and an outer polymeric layer of nylon 12 (Rilsan AESNO or Pebax 7233/7033). A metal wire braid layer was optionally included between the inner and middle polymeric layers, or between the middle and outer polymeric layers. Use of the PVDF homopolymer as the inner polymeric layer provided low frictional resistance to any components moving through the central lumen of the shaft. Relatively, the inner polymeric layer of PVDF homopolymer provided a layer with a lubricity greater than that associated with a polar polymer, such as nylon.

Example 7

Catheter Shaft Embodiment

A catheter shaft $26^A$ was constructed in accordance with the embodiment illustrated in FIG. 5. The catheter shaft $26^A$ includes a proximal segment $27^A$, a distal segment $29^A$ and a transitional segment $28^A$ smoothly tethering the proximal segment $27^A$ and the distal segment $29^A$. A reinforcing spring extends within the inner polymeric layers $30^A$, $30^B$, $30^C$ of the shaft $26^A$ from the proximal segment $27^A$, through the transitional segment $28^A$ and into a proximal portion of the distal segment $29^A$, so as to enhance the torqueability and column strength of the shaft and kink resistance. A protective shrink tube $36^A$ (preferably PVDF) is placed around a distal end of a reinforcing spring $34^A$ to alleviate stress rise that may be produced by sudden changes in internal shaft $26^A$ structure.

The inner polymeric layer of proximal segment $27^A$, transitional segment $28^A$, and distal segment $29^A$ is the same polymeric tube extruded from functionalized PVDF (e.g., KYNAR ADX®). The middle polymeric layers $31^A$, $31^B$, $31^C$ are different for different shaft segments. The middle polymer layers $31^A$, $31^B$, $31^C$ consist of nylon 12 (Pebax 7233SA01 or AESNO) filled with 30% wt. barium sulfate for the proximal segment $27^A$, Pebax 5533SA01 filled with 30% wt. barium sulfate in the transitional segment $28^A$, and Pebax 3533SA01 filled with 40% wt. barium sulfate in the distal segment $29^A$. The distal segment $29^A$ is mechanically flexible and deflectable via an internal manipulation mechanism embedded within the shaft and extended proximally to the catheter handle (not shown here). The different polymers in the middle polymeric layers $31^A$, $31^B$, $31^C$ are primarily to achieve increasing mechanical flexibility from the proximal to the distal ends of the shaft $26^A$. The outer polymeric layers $32^A$, $32^B$, $32^C$ are formed from a same tube extruded from functionalized PVDF, such as KYNAR ADX®. The outer polymeric layers $32^A$, $32^B$, $32^C$ provide good hydrophobic barrier properties against body fluids or medical fluids and surface lubricity when the catheter shaft $26^A$ is manipulated through the vasculature system. At the same time, the functionalized PVDF outer polymeric layers $32^A$, $32^B$, $32^C$ allow for good adhesions with the polar middle polymer layers $31^A$, $31^B$, $31^C$. A metal wire braid layer $33^A$ extends from the proximal segment $27^A$ to the portion of the transitional segment $29^A$ or the deflectable distal segment $29^A$, and can be reliably embedded into the middle polymer layers $31^A$, $31^B$, $31^C$. Also, the inner polymeric layers $30^A$, $30^B$, $30^C$ of the lubricious PVDF polymer allows for smooth passage of other medical devices during clinical uses. Relatively, the inner and outer polymeric layers of functionalized PVDF provided layers with lubricities greater than that associated with a polar polymer, such as nylon.

The deflectable distal segment $29^A$ of a catheter shaft $26^A$ plays an important role in the successes of medical procedures. Its mechanical performances during clinical procedures are of critical importance to manual manipulation of catheter devices, to a physician's feel, and to get easy accesses to human anatomy for delivering medical therapy on targeted anatomical sites. It is highly desirable to maintain the mechanical performances of the deflectable distal segment $29^A$ of the catheter shaft $26^A$ during the course of a medical procedure. On the other hand, due to its bulky structure, the distal segment $29^A$ of the catheter shaft $26^A$ can generally fulfill various clinical requirements on its mechanical performances. Therefore, to maintain the optimum and consistent mechanical strengths of catheter shafts within aqueous environments (consisting of body fluids and medical agents such as saline), the deflectable distal segment and transitional segment should be self-protected from the adverse influences on its mechanical performances arising from body fluids and medical agents.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician (or to a robotic control configured to manipulate the device) and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A catheter comprising the following:
   an elongated structure, wherein the elongated structure has a distal portion, a proximal portion, and a tie band coupled between the distal portion and the proximal portion:
   a handle operably connected to a proximal end of the proximal portion of the elongated structure; and
   wherein the distal portion comprises a shaft, wherein the shaft comprises three radially positioned polymeric layers that include an inner layer, a middle layer, and an outer layer, wherein at least two of the three layers include chemically dissimilar polymers and the outer layer of the distal portion is formed from a nonpolar polymer, and wherein an outer layer of the tie band is formed from functionalized polyvinylidene fluoride (PVDF) and an outer layer of the proximal portion is formed from a polar polymer.

2. The catheter of claim 1, wherein the functionalized PVDF comprises polyvinylidene homopolymer grafted with maleic anhydride.

3. The catheter of claim 1, wherein the functionalized PVDF comprises vinylidene and hexafluoropropylene grafted with maleic anhydride.

4. A catheter shaft configured to be inserted into a patient's body, the catheter shaft comprising the following:
   an elongated structure, wherein the elongated structure has a distal portion, a proximal portion, and a tie band disposed between the distal portion and the proximal portion;
   a handle operably connected to the proximal end of the proximal portion; and
   wherein the distal portion comprises a shaft, wherein the shaft comprises an inner polymeric layer; a middle polymeric layer bonded to the inner polymeric layer; and an outer polymeric layer bonded to the middle polymeric layer, wherein the outer polymeric layer is formed from a hydrophobic polymer, and wherein an outer layer of the tie band is formed from functionalized polyvinylidene fluoride (PVDF) and an outer layer of the proximal portion is formed from a hygroscopic polymer.

5. The catheter shaft of claim 4, wherein the inner layer of the distal portion comprises PVDF homopolymer, the middle layer of the distal portion comprises PVDF copolymer, and the outer layer of the distal portion comprises the functionalized PVDF.

6. The catheter shaft of claim 4, wherein the inner layer of the distal portion comprises the PVDF homopolymer, the middle layer of the distal portion comprises the functionalized PVDF, and the outer layer of the distal portion comprises the PVDF homopolymer.

7. The catheter shaft of claim 4, wherein the inner layer of the distal portion comprises the PVDF copolymer, the middle layer of the distal portion comprises the functionalized PVDF, and the outer layer of the distal portion comprises the PVDF copolymer.

8. The catheter shaft of claim 7, wherein the PVDF copolymer comprises a copolymer of vinylidene fluoride with hexafluoropropylene.

9. The catheter shaft of claim 4, wherein the inner polymeric layer of the distal portion comprises the functionalized PVDF, the middle polymeric layer of the distal portion comprises a polyamide, and the outer polymeric layer of the distal portion comprises the functionalized PVDF.

10. The catheter shaft of claim 9, wherein the polyamide is selected from the group consisting of nylon 11, nylon 12, and combinations thereof.

11. The catheter shaft of claim 4, wherein the inner polymeric layer of the distal portion comprises nylon, the middle polymeric layer of the distal portion comprises the functionalized PVDF, and the outer polymeric layer of the distal portion comprises the PVDF copolymer.

12. The catheter shaft of claim 4, wherein the inner polymeric layer of the distal portion comprises the PVDF homopolymer, the middle polymeric layer of the distal portion comprises the functionalized PVDF, and the outer polymeric layer of the distal portion comprises nylon.

13. The catheter shaft of claim 12, wherein the nylon is selected from the group consisting of nylon 11, nylon 12, and combinations thereof.

14. The catheter shaft of claim 4, further comprising a metal wire braid layer proximate to an interface of the inner and middle polymeric layers of the distal portion.

15. The catheter shaft according to claim 4, further comprising a metal wire braid layer proximate to a junction of the middle and outer polymeric layers of the distal portion.

16. A catheter shaft, comprising the following:
   a proximal segment;
   a handle operatively connected to the proximal segment;
   a transitional segment; and a distal segment;
wherein each of the proximal segment, the transitional segment, and the distal segment has an inner polymeric layer, a middle polymeric layer, and an outer polymeric layer, wherein the outer polymeric layer of the transitional segment is formed of functionalized polyvinylidene fluoride (PVDF), wherein at least one of the inner and middle polymeric layers in the distal segment is formed of functionalized PVDF, and the outer polymeric layer of the distal segment is formed of a nonpolar polymer and the outer polymeric layer of the proximal segment is formed of a polar polymer.

17. The catheter shaft of claim 16, wherein the inner polymeric layer of each segment is formed of the functionalized PVDF.

18. The catheter shaft of claim 16, wherein the middle polymeric layer of each segment is formed from a polymer selected from the group consisting of a poly (ether block amide), a polyamide, and combinations thereof.

19. The catheter shaft of claim 16, further comprising a reinforcing spring extending along the inner polymeric layer from the proximal segment and through a portion of the distal segment.

20. The catheter shaft according to claim 19, further comprising a shrink tube placed around a distal end of the reinforcing spring configured to alleviate stress rise therefrom.

21. The catheter shaft of claim 16, wherein the middle polymer layer is formed of different polymers between the proximal segment, the transitional segment, and the distal segment.

22. The catheter shaft of claim 21, wherein a flexibility of the middle polymeric layer increases from the proximal segment to the distal segment.

23. The catheter shaft of claim 22, wherein each one of the inner polymeric layer, the middle polymeric layer, and the outer polymeric layer of the proximal segment are formed from at least one type of polyamide.

24. The catheter shaft of claim 23, wherein the inner polymer layer of the transitional segment and the distal segment are formed from the at least one type of polyamide.

25. The catheter shaft of claim 24, further comprising a tie band between the proximal segment and the transitional segment, wherein the tie band comprises an inner polymeric layer formed of the at least one polyamide and a middle polymeric layer and outer polymeric layer formed of the functionalized PVDF.

26. The catheter shaft of claim 25, wherein the transitional segment and the distal segment each has an inner polymeric layer formed of the at least one type of polyamide, a middle polymeric layer formed of a functionalized PVDF, and an outer polymeric layer formed of a polymer selected from the group consisting of PVDF homopolymer and PVDF copolymer.

* * * * *